United States Patent
Lipchitz et al.

(10) Patent No.: US 8,377,089 B2
(45) Date of Patent: Feb. 19, 2013

(54) MEDICAL CANNULA ASSEMBLY

(75) Inventors: John Lipchitz, Billerica, MA (US);
Justin Dye, Mansfield, MA (US); Rod Berube, North Attleboro, MA (US);
Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 887 days.

(21) Appl. No.: 11/931,335

(22) Filed: Oct. 31, 2007

(65) Prior Publication Data

US 2008/0058723 A1    Mar. 6, 2008

Related U.S. Application Data

(63) Continuation of application No. 10/805,380, filed on Mar. 22, 2004, now abandoned.

(51) Int. Cl.
*A61B 17/34* (2006.01)

(52) U.S. Cl. .................. 606/185; 606/108; 600/184

(58) Field of Classification Search .............. 606/185, 606/104, 170, 108, 180, 184, 190; 604/264, 604/167.01–167.04, 506, 164.01, 164.02, 604/164.11, 167.06
See application file for complete search history.

(56) References Cited

U.S. PATENT DOCUMENTS

| 4,573,448 A | 3/1986 | Kambin |
| 5,104,383 A | 4/1992 | Shichman |
| 5,197,955 A | 3/1993 | Stephens et al. |
| 5,209,737 A | 5/1993 | Ritchart et al. |
| 5,256,149 A | 10/1993 | Banik et al. |
| 5,258,003 A | 11/1993 | Ciaglia et al. |
| 5,308,336 A | 5/1994 | Hart et al. |
| 5,318,585 A | 6/1994 | Guy et al. |
| 5,380,288 A | 1/1995 | Hart et al. |
| 5,383,860 A * | 1/1995 | Lau .................. 604/167.03 |
| 5,385,553 A | 1/1995 | Hart et al. |
| 5,407,433 A | 4/1995 | Loomas |
| 5,411,483 A | 5/1995 | Loomas et al. |
| 5,456,673 A | 10/1995 | Ziegler et al. |

(Continued)

FOREIGN PATENT DOCUMENTS

| DE | 29717940 U1 | 1/1998 |
| DE | 19955071 C1 | 4/2001 |

(Continued)

OTHER PUBLICATIONS

"Caps-Lock Cannula System" http://www.atlantech-md.co.uk/products/shoulder/shoulder1.html (Oct. 6, 2003).

(Continued)

*Primary Examiner* — Ryan Severson
*Assistant Examiner* — Rachel S Papeika
(74) *Attorney, Agent, or Firm* — Fish & Richardson P.C.

(57) ABSTRACT

A medical assembly includes a cannula and a sealing cap releasably coupled to the cannula. The cap includes a body and a sealing member integrally molded with the body to form a fluid-tight seal between the cap and cannula. The cap includes a member defining an opening for passage of a medical instrument therethrough in a fluid-tight manner. The member includes a first portion surrounding the opening and being thickened to limit tearing of the first portion, and a second portion surrounding the first portion being tapered down in thickness toward the first portion to increase flexibility of the member. The assembly includes a shaft receivable in a lumen defined by an inner surface of the cannula. The shaft includes a protrusion and the inner surface further defines a protrusion receiving formation.

22 Claims, 12 Drawing Sheets

U.S. PATENT DOCUMENTS

| | | | |
|---|---|---|---|
| 5,476,475 A | | 12/1995 | Gadberry |
| 5,496,289 A | * | 3/1996 | Wenstrom, Jr. ............... 604/264 |
| 5,531,758 A | | 7/1996 | Uschold et al. |
| 5,545,142 A | | 8/1996 | Stephens et al. |
| 5,554,124 A | | 9/1996 | Alvarado |
| 5,556,411 A | | 9/1996 | Taoda et al. |
| 5,569,205 A | | 10/1996 | Hart et al. |
| 5,591,190 A | | 1/1997 | Yoon |
| 5,603,702 A | | 2/1997 | Smith et al. |
| 5,628,732 A | | 5/1997 | Antoon et al. |
| 5,634,908 A | | 6/1997 | Loomas |
| 5,707,362 A | | 1/1998 | Yoon |
| 5,735,867 A | | 4/1998 | Golser et al. |
| 5,752,936 A | | 5/1998 | Chen |
| 5,772,678 A | | 6/1998 | Thomason et al. |
| 5,792,113 A | | 8/1998 | Kramer et al. |
| 5,807,338 A | | 9/1998 | Smith et al. |
| 5,820,606 A | | 10/1998 | Davis et al. |
| 5,827,228 A | | 10/1998 | Rowe |
| 5,865,807 A | | 2/1999 | Blake |
| 5,882,344 A | * | 3/1999 | Stouder, Jr. ................. 604/264 |
| 5,895,377 A | | 4/1999 | Smith et al. |
| 5,904,699 A | | 5/1999 | Schwemberger et al. |
| 5,957,888 A | * | 9/1999 | Hinchliffe ................. 604/117 |
| 6,110,185 A | | 8/2000 | Barra et al. |
| 6,228,061 B1 | | 5/2001 | Flatland et al. |
| 6,482,181 B1 | | 11/2002 | Racenet et al. |
| 2005/0033342 A1 | | 2/2005 | Hart et al. |

FOREIGN PATENT DOCUMENTS

| | | | |
|---|---|---|---|
| EP | 346469 A4 | | 7/1990 |
| EP | 567141 A3 | | 1/1994 |
| EP | 653222 A1 | | 5/1995 |
| EP | 538060 B1 | | 9/1995 |
| EP | 716862 A1 | | 6/1996 |
| EP | 724865 A1 | | 8/1996 |
| EP | 784961 A1 | | 7/1997 |
| EP | 873721 A2 | | 10/1998 |
| EP | 696459 B1 | | 11/1998 |
| EP | 591851 B1 | | 6/1999 |
| EP | 1127550 A1 | | 8/2001 |
| EP | 1219251 A1 | | 7/2002 |
| EP | 1219252 A1 | | 7/2002 |
| EP | 1219253 A1 | | 7/2002 |
| EP | 1269926 A1 | | 1/2003 |
| EP | 1269925 B1 | | 12/2003 |
| EP | 1262150 B1 | | 3/2004 |
| EP | 1219250 B1 | | 11/2004 |
| SU | 1521465 A1 | | 11/1989 |
| WO | WO9325148 A1 | | 12/1993 |
| WO | WO9507663 A1 | | 3/1995 |
| WO | WO9836785 A1 | | 8/1998 |
| WO | WO 9836785 A1 | * | 8/1998 |
| WO | WO9853865 A1 | | 12/1998 |
| WO | WO9921601 A1 | | 5/1999 |
| WO | WO9929242 A1 | | 6/1999 |
| WO | WO0054679 A1 | | 9/2000 |
| WO | WO0162167 A1 | | 8/2001 |
| WO | WO0191653 A2 | | 12/2001 |
| WO | WO0230305 A3 | | 6/2002 |
| WO | WO03020140 A1 | | 3/2003 |
| WO | WO03043683 A1 | | 5/2003 |

OTHER PUBLICATIONS

"SPS™—The Karl Storz Secure Portal System", ENDOWORLD OSM-21, Karl Storz-Sports Medicine, Inc. (Jan. 2003).
Stephen J. Snyder, M.D., "Crystal™ Cannula" Endoscopic Carpal Tunnel Release System, http://www.arthrex.com/English/private/featured_product_november.phtml (May 2, 2002).
"Translucent Twist-In Cannula System" Arthrex, http://www.arthrex.com/English/private/catalog/11/11-2.htm (Sep. 17, 2002).
"Instrument Cannula" Arthrex, http://www.arthrex.com/English/private/catalog/11/11-3.htm (Sep. 17, 2002).
"Crystal™ Cannula" Arthrex, http://www.arthrex.com/English/private/catalog/11/11-1.htm (Sep. 17, 2002).
"Clear Cannula System" Mitek Products (Jun. 2000).
"Applied Premium Disposable Trocar System" Applied Medical (2000).
"Entry Systems Inflow Devices and Accessories" Linvatec (undated).
"Products The Main Genicon Products Catalog" http://www.genicon.co.uk/products.html (Sep. 18, 2002).
"A New Disposable Cannula for Shoulder Arthroscopy" "Small Joint Arthroscopy Instruments" Arthroscopic Instruments, Linvatec Source (undated).
International Search Report for PCT/US2005/009267, filed Mar. 21, 2005 dated Jul. 26, 2005.
Written Opinion for PCT/US2005/009267, filed Mar. 21, 2005 dated Jul. 26, 2005.
European Patent Office, Supplementary Partial European Search Report for PCT application No. PCT/US01/45567.

* cited by examiner

MEDICAL CANNULA ASSEMBLY

CROSS-REFERENCE TO RELATED APPLICATIONS

This application is a continuation of U.S. patent application Ser. No. 10/805,380 filed on Mar. 22, 2004. The disclosure of this prior application is incorporated by reference in its entirety.

TECHNICAL FIELD

This invention relates to a cannula used for arthroscopic, endoscopic, or laproscopic surgery.

BACKGROUND

A cannula can be inserted into a portal in a tissue in cooperation with an obturator or trocar that is received in the cannula and has a tapered end that extends beyond the end of the cannula. Once the cannula has been inserted into the tissue, the obturator or trocar is removed and surgical instruments can be passed through the cannula into tissue to perform arthroscopic, endoscopic, or laproscopic surgery.

SUMMARY

According to one aspect of the invention, a medical assembly includes a cannula and a sealing cap releasably coupled to the cannula. The cannula and cap are configured to form a fluid-tight seal therebetween without the use of an additional element. Embodiments of this aspect of the invention may include one or more of the following features: The cannula has a wall with an inner surface defining a lumen, and the assembly further includes a shaft receivable in the lumen. The shaft includes a protrusion and the inner surface further defines a protrusion receiving formation, e.g., a slot.

The cap includes a body and a sealing member integrally molded with the body. The sealing member is, e.g., chemically bonded with the body. The cannula includes an annular shoulder and the sealing member includes an annular projection that is compressed against the annular shoulder to form the fluid-tight seal. The cannula defines a slot, e.g., a J-shaped slot, and the cap has a projection receivable in the slot to releasably couple the cap to the cannula.

The cap includes a member defining an opening for passage of a medical instrument therethrough in a fluid-tight manner. The member includes, e.g., a first portion surrounding the opening that is thickened to limit tearing of the first portion, and a second portion surrounding the first portion that is tapered down in thickness toward the first portion to increase flexibility of the member. According to another aspect of the invention, a medical assembly includes a cannula and a sealing cap releasably coupled to the cannula. The cap includes a body and a sealing member that is integrally molded with the body and configured to form a fluid-tight seal with the cannula.

According to another aspect of the invention, a medical assembly includes a shaft with a protrusion, and a cannula having a wall with an inner surface defining a lumen for receiving the shaft. The inner surface defines a protrusion receiving formation, e.g., a slot extending from a proximal end of the cannula. Embodiments of this aspect of the invention may include one or more of the following features. The shaft includes a second, opposing protrusion and the inner surface defines a second, opposing protrusion receiving formation, e.g., a second slot. The second protrusion receiving formation extends from the proximal end of the cannula. The lumen has, e.g, a constant diameter or is tapered.

According to another aspect of the invention, a medical cannula includes a wall with an inner surface defining a lumen. The inner wall defines a protrusion receiving formation, e.g., a slot, extending from a proximal end of the cannula.

Embodiments of this aspect of the invention may include one or more of the following features. The inner surface defines a second, opposing protrusion receiving formation, e.g., a second slot. The second protrusion receiving formation extends from the proximal end of the cannula. The wall has an outer surface defining an outer slot, e.g., a J-shaped slot, and a second, opposing outer slot, e.g., a second J-shaped slot. The medical cannula further includes an annular shoulder coupled to the wall for forming a fluid-tight seal with a cap. The wall has an outer surface that is threaded. The lumen has, e.g, a constant diameter or is tapered.

According to another aspect of the invention, a sealing cap includes a body for releasable attachment to a medical cannula and a sealing member integrally formed with the body and configured to form a fluid-tight seal with the cannula without the use of an additional element.

Embodiments of this aspect of the invention may include one or more of the following features. The sealing member is, e.g., chemically bonded with the body. The sealing member includes an annular projection that is compressible against the medical cannula to form the fluid-tight seal. The cap includes a projection for removably connecting the cap to the cannula. The cap includes an outer seal disposed over the body. The outer seal defines an opening for passage of a medical instrument therethrough in a fluid-tight manner. The outer seal includes a first portion surrounding the opening that is thickened to limit tearing of the first portion, and a second portion surrounding the first portion that is tapered down in thickness toward the first portion to increase flexibility of the member. The cap further includes an inner seal disposed within the outer seal. The inner seal includes an opening for passage of the medical instrument therethrough in a fluid tight manner.

According to another aspect of the invention, a seal includes a member defining an opening for passage of a medical instrument therethrough in a fluid-tight manner. A first portion of the member surrounds the opening and is thickened to limit tearing of the first portion. A second portion of the member surrounds the first portion and is tapered down in the thickness toward the first portion to increase flexibility of the member.

According to another aspect of the invention, a shaft includes an elongated body receivable in a medical cannula. At least two opposed protrusions extend from the body and are configured to mate with respective protrusion receiving formations in the cannula.

According to another aspect of the invention, a medical assembly includes a means for forming a channel for inserting a surgical instrument into a tissue, and a means for forming a fluid-tight seal with the means for forming a channel.

According to another aspect of the invention, a method includes inserting a cannula into tissue, and removing a sealing cap from the cannula as a single unit without leaving a loose element behind. Embodiments of this aspect of the invention may include one or more of the following features: removing tissue through the cannula after removing the sealing cap, and reattaching the cap to the cannula while the cannula remains in the tissue.

Advantages of the invention may include one or more of the following. The integral sealing member allows the cap to be removed from the cannula without the risk of the sealing member being separated from the cap. The integral sealing member also allows the cap to be reattached to the cannula without distorting the sealing member. The protrusions on the shaft and the corresponding protrusion receiving formations in the cannula facilitate the coupling of the shaft to the cannula such that a user can apply a torque to the shaft to turn the cannula. The thickened portion and the tapered portion of the outer seal facilitate the insertion of large surgical instruments through the cannula in a fluid-tight manner.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
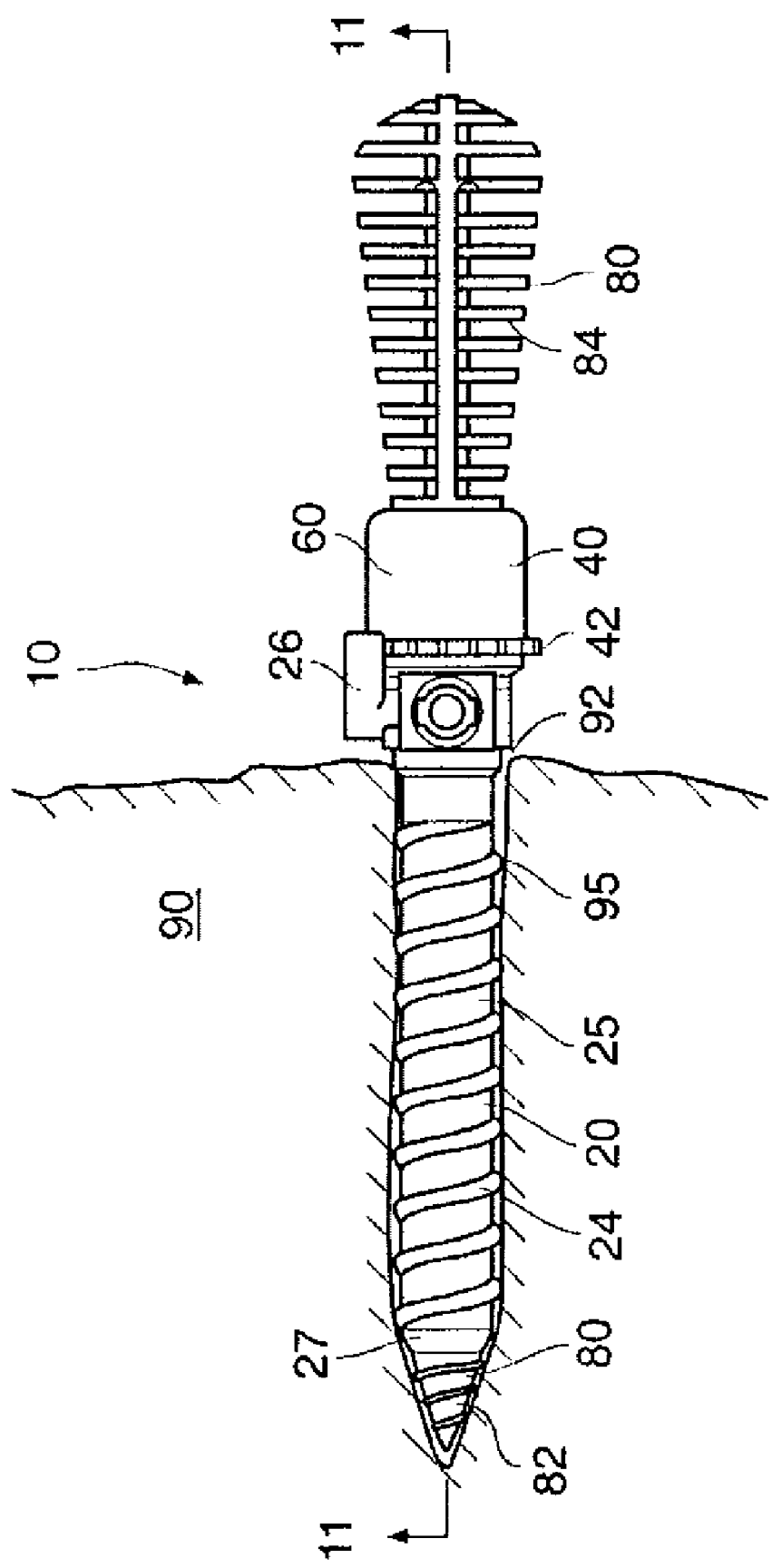
FIG. 1 is a side view of a medical assembly shown advanced into tissue.

Referring to FIG. 1, a medical assembly 10 includes a threaded cannula 20, a sealing cap 40 removably coupled to cannula 20, and a shaft, e.g., a trocar or obturator 80, which is received within cannula 20 and cap 40. Obturator 80 includes a tapered, threaded distal end 82 that extends beyond a distal end 27 of cannula 20, and a proximal handle 84 that abuts against cap 40. Obturator 80 is coupled to cannula 20, as described below, such that turning proximal handle 84 of obturator 80 turns cannula 20 to insert cannula 20 into tissue 90. When coupled, cap 40 and cannula 20 form a fluid-tight seal without the use of an additional sealing element, e.g., an O-ring, such that cap 40 can be removed from and re-coupled to cannula 20 by the user without the possibility of losing or dropping such an additional sealing element. The removal of cap 40 from cannula 20 permits, e.g., the removal of large pieces of tissue through cannula 20.

Figure 2A:
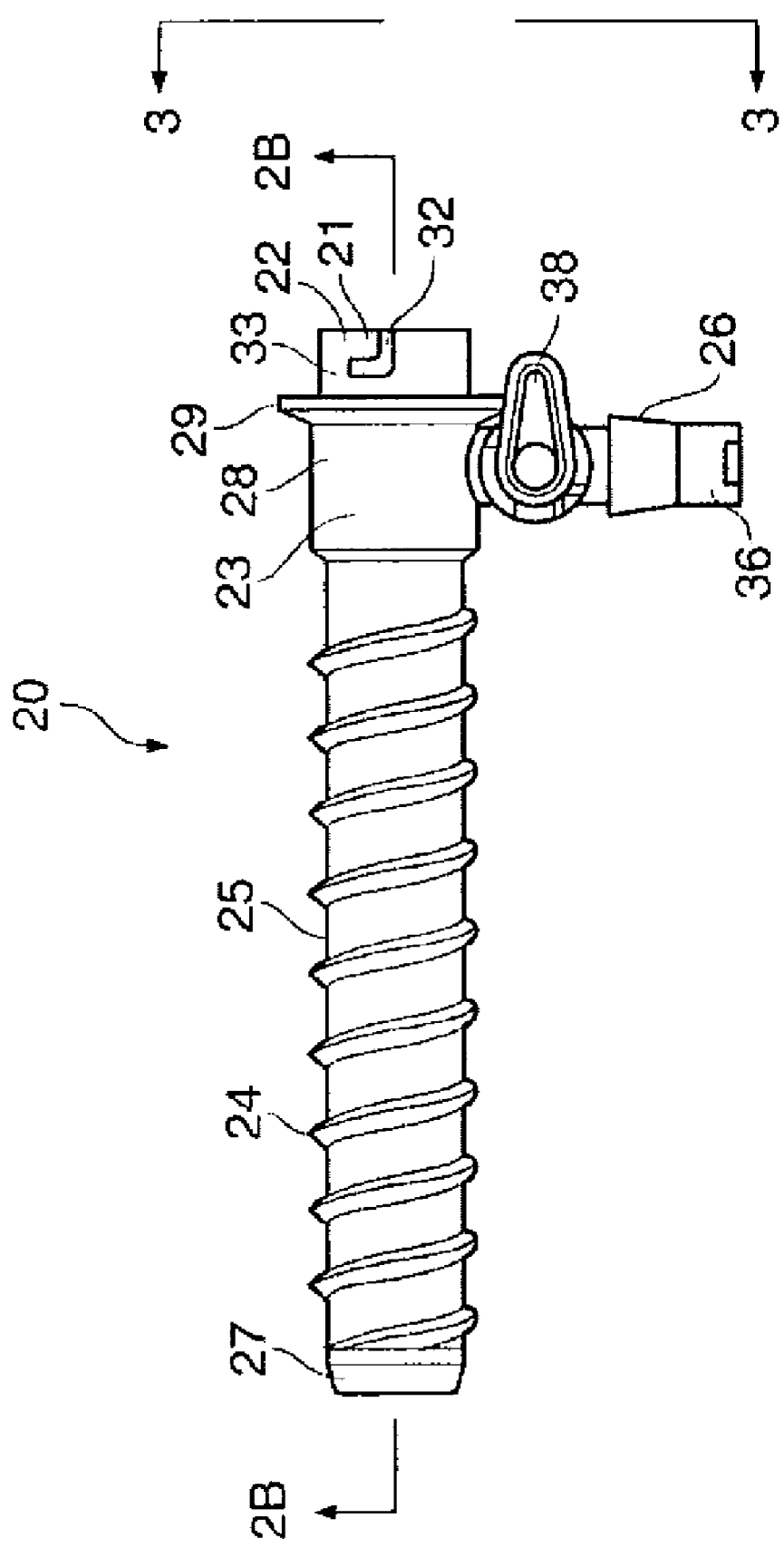
FIG. 2A is a side view of a cannula of the assembly of FIG. 1.
Figure 2B:
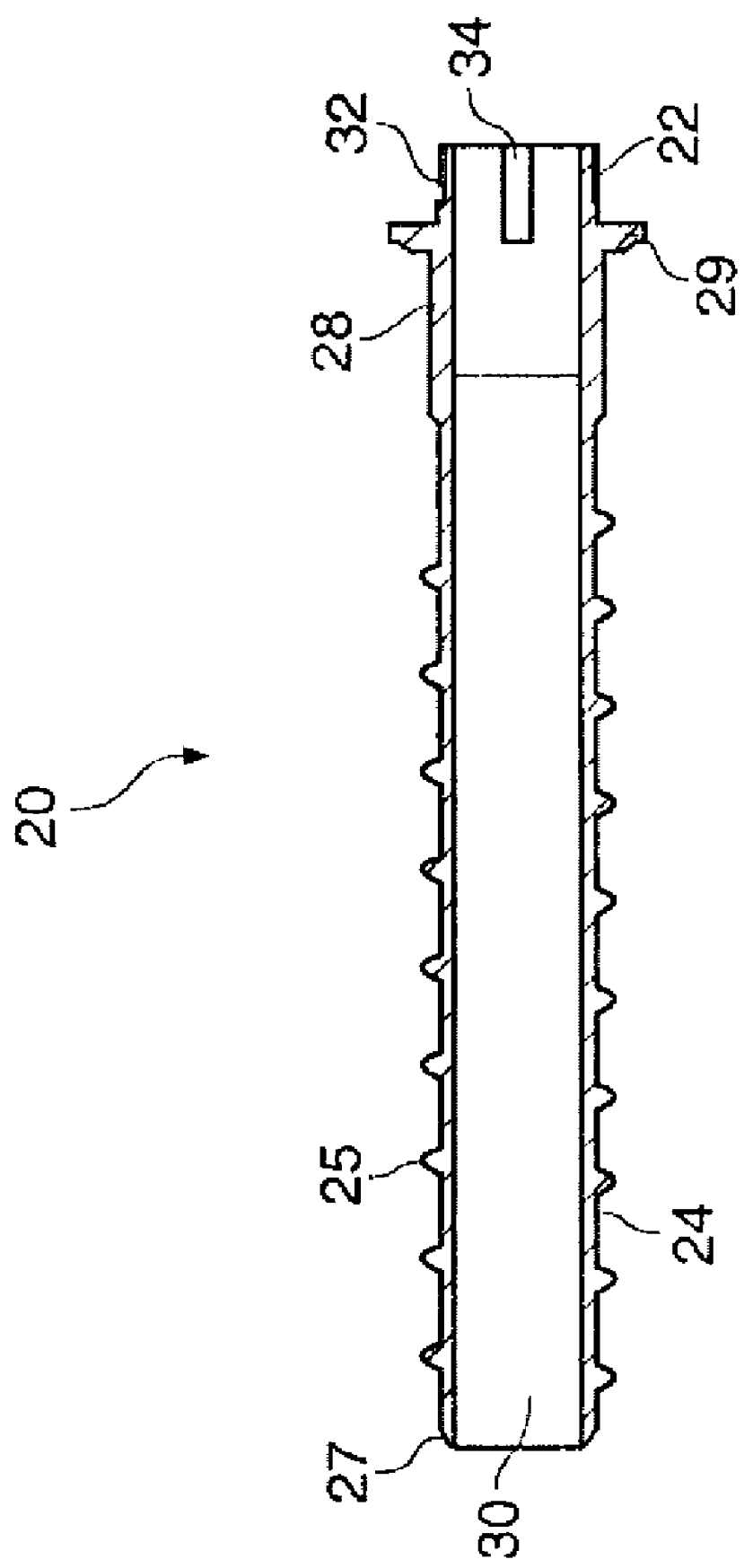
FIG. 2B is a cross-sectional view of the cannula of FIG. 2A along line 2B-2B.
Figure 3:
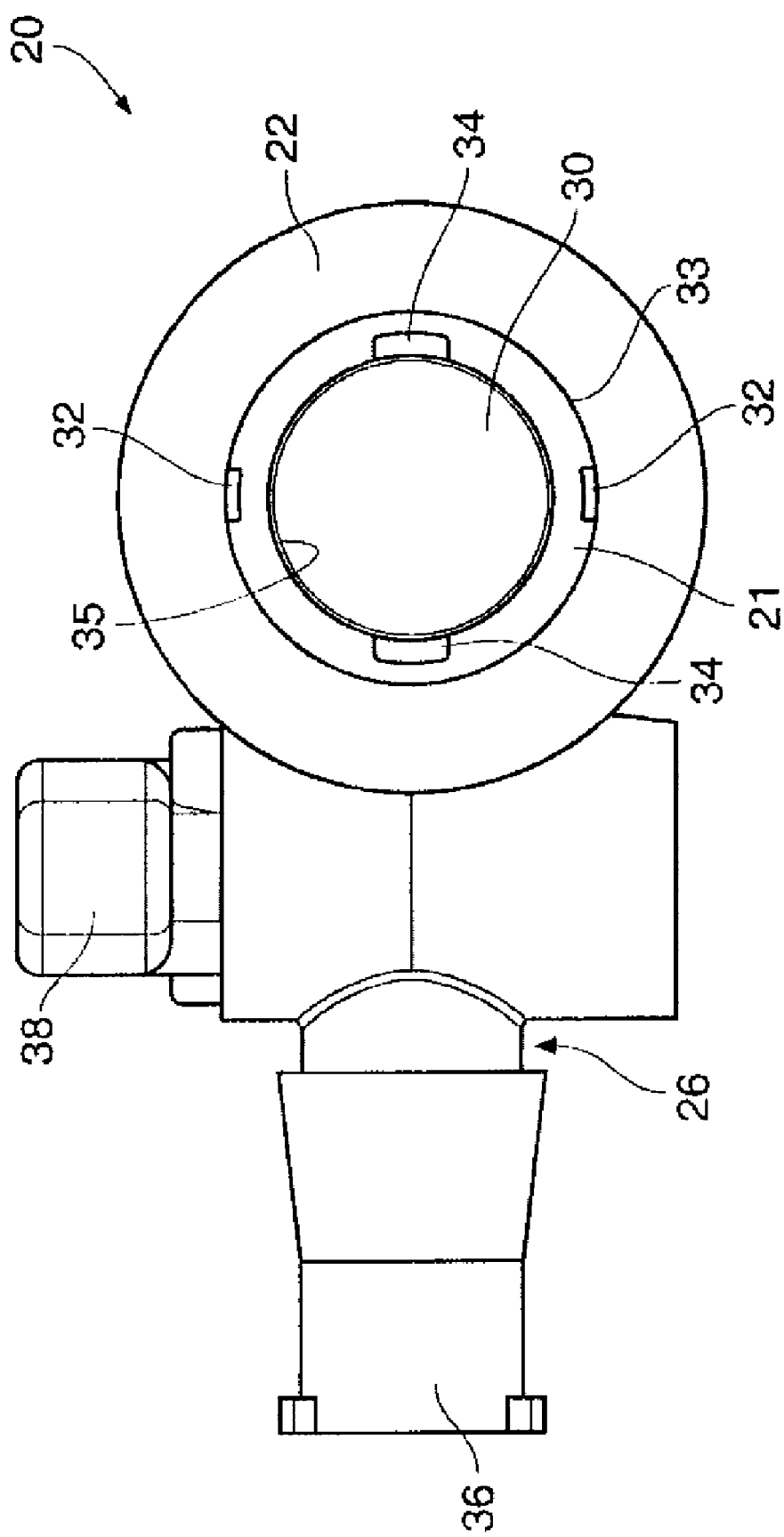
FIG. 3 is an end view of the cannula of FIG. 2 along line 3-3.

Referring to FIGS. 2A, 2B, and 3, cannula 20 includes a proximal portion 22, a stopcock portion 28, a threaded distal portion 25, and tapered distal end 27, with a longitudinal bore or lumen 30 extending the length of cannula 20. Proximal portion 22 has a cylindrical wall 21 with mating features 32, 34 formed in outer and inner surfaces 33, 35, respectively, of wall 21. Mating features 32 are, e.g., opposing J-shaped slots for releasably locking cap 40 to cannula 20, as discussed below. Mating features 35 are, e.g., opposing protrusion receiving formations, such as opposing longitudinal slots 34 for receiving corresponding projections on obturator 80, as discussed below. Between proximal portion 22 and stopcock portion 28 is an annular shoulder 29 for forming a fluid-tight seal with cap 40, as discussed below. Stopcock portion 28 includes a cylindrical portion 23 defining a section of bore 30, and a stopcock 26 in communication with bore 30 for aspirating fluid into bore 30 or for applying suction to bore 30. Stopcock 26 includes a port 36 for attachment to a source of fluid aspiration or suction and a manually actuatable valve 38 for controlling the amount of fluid flow or suction.

Distal threaded portion 25 of cannula 20 includes threads 24 that facilitate inserting cannula 20 into tissue 90 by lifting the skin as the cannula is inserted into tissue 90. Threads 24 also limit cannula 20 from pulling out of tissue 90 once cannula 20 has been inserted. Tapered distal end 27 also facilitates inserting cannula 20 into tissue 90 by gradually expanding the size of a portal 92 (FIG. 1) in tissue 90.

Distal end 27 has a length of approximately 2.5 mm and is tapered at an angle of approximately 15 degrees from the center line, with the length and taper angle chosen for manufacturability. Distal threaded portion 25 has a length of approximately 40 to 90 mm, an outer diameter of approximately 4.5 to 12 mm, with a thread depth of approximately 0.5 to 1.5 mm, a thread angle of approximately 60 degrees, and approximately 0.17 threads per mm. The length is selected according to the depth of the tissue being accessed. Cylindrical portion 23 of stopcock portion 28 has a length of approximately 13.5 mm and an outer diameter of approximately 9 mm. Proximal portion has a length of approximately 5 mm and an outer diameter of approximately 11 mm, to facilitate mating with cap 40, as discussed below. Longitudinal bore 30 has a length of approximately 60 to 105 mm and a diameter of approximately 2.5 to 10 mm. The length of bore 30 varies according to the length of distal threaded portion 25. Longitudinal bore 30 and distal threaded portion 25 each has a constant diameter or is tapered, e.g., at an angle of approximately 0.125 to 2 degrees, to facilitate manufacturing by molding. Longitudinal slots 34 each have a length of approximately 6.5 mm and a width of approximately 2 mm to facilitate mating with wings of obturator 80, as described below.

Figure 4:
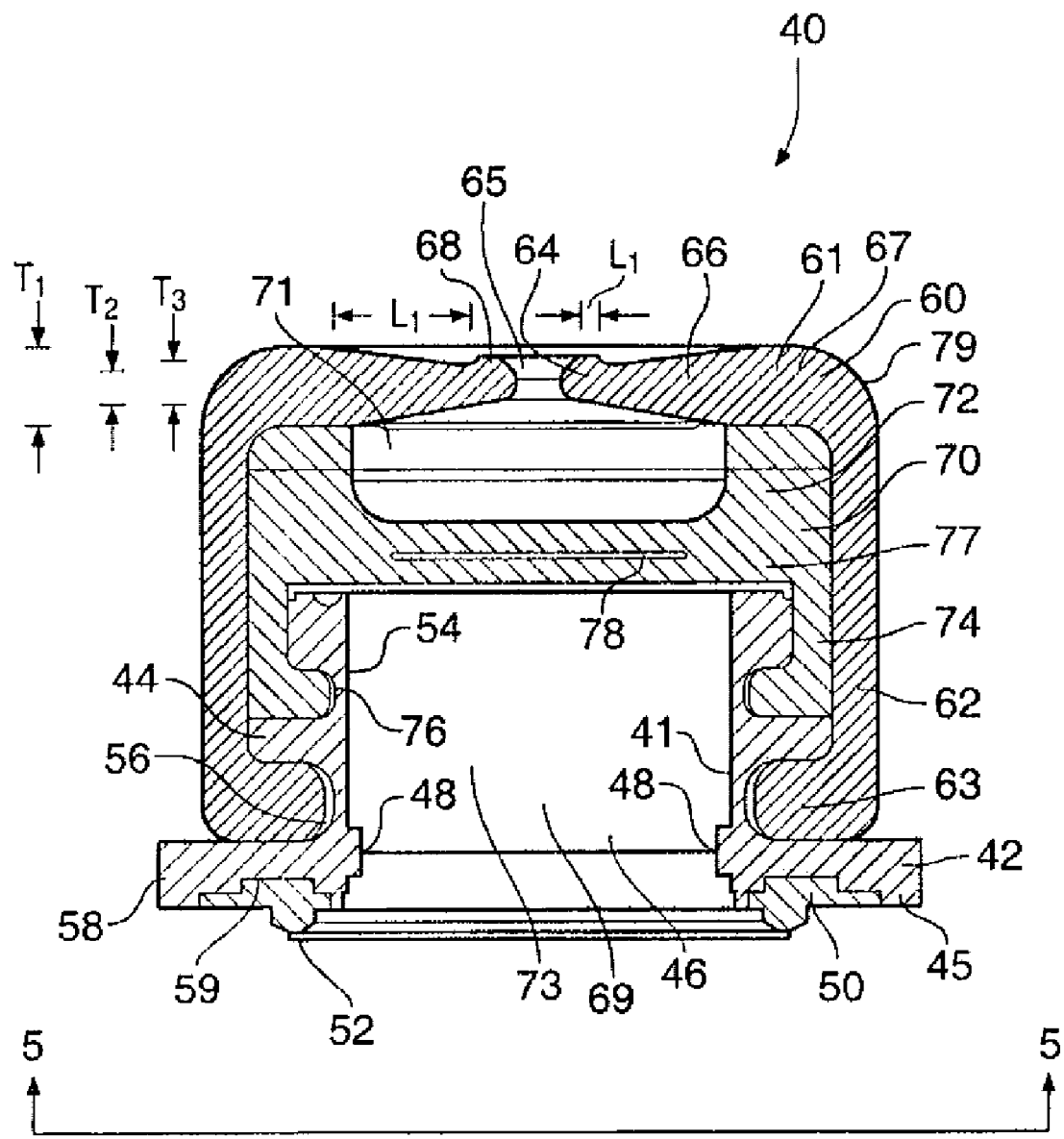
FIG. 4 is a cross-sectional view of the removable sealing cap of the assembly of FIG. 1.
Figure 5:
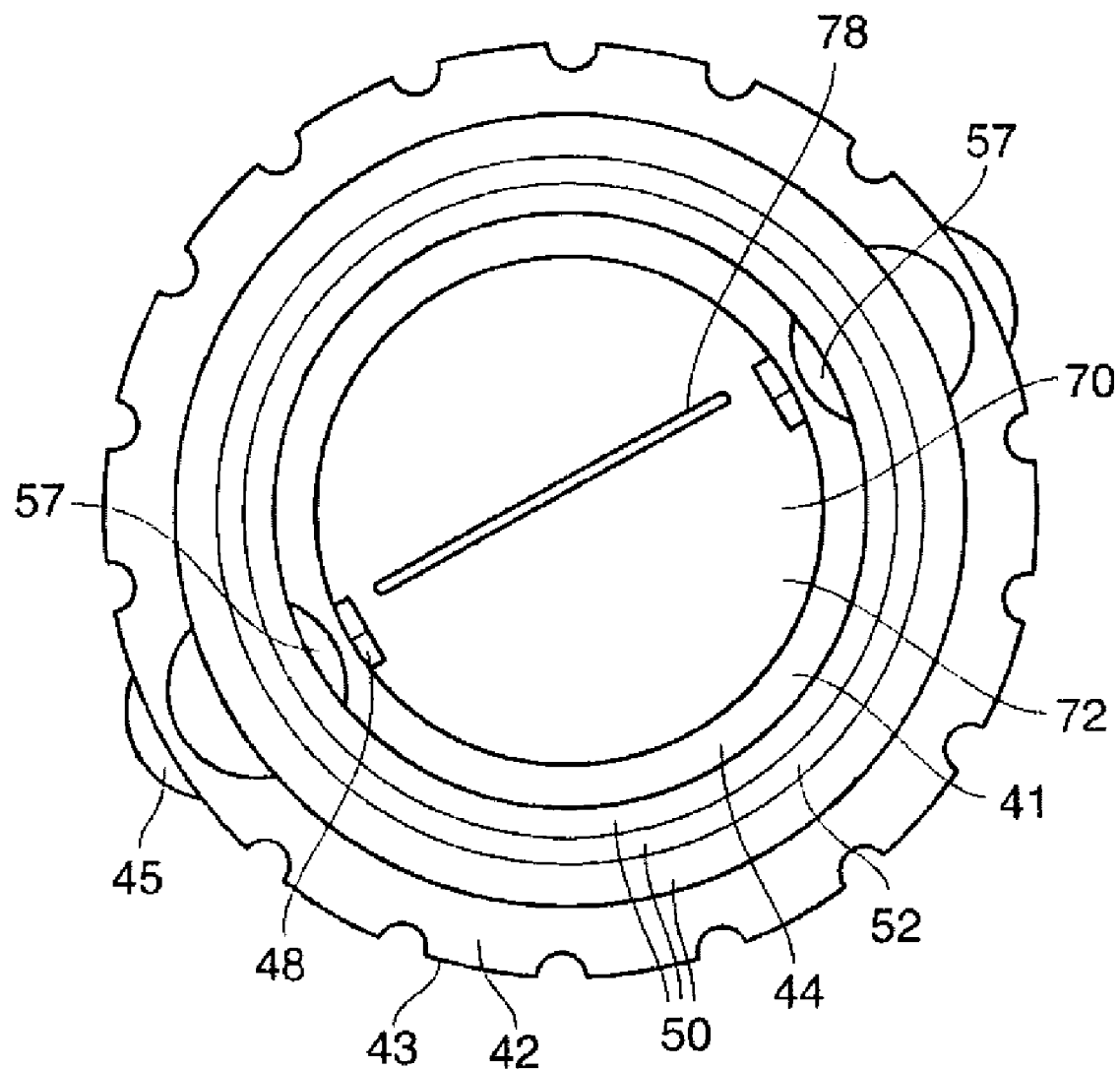
FIG. 5 is an end view of the cap of FIG. 4 along line 5-5.
Figure 6:
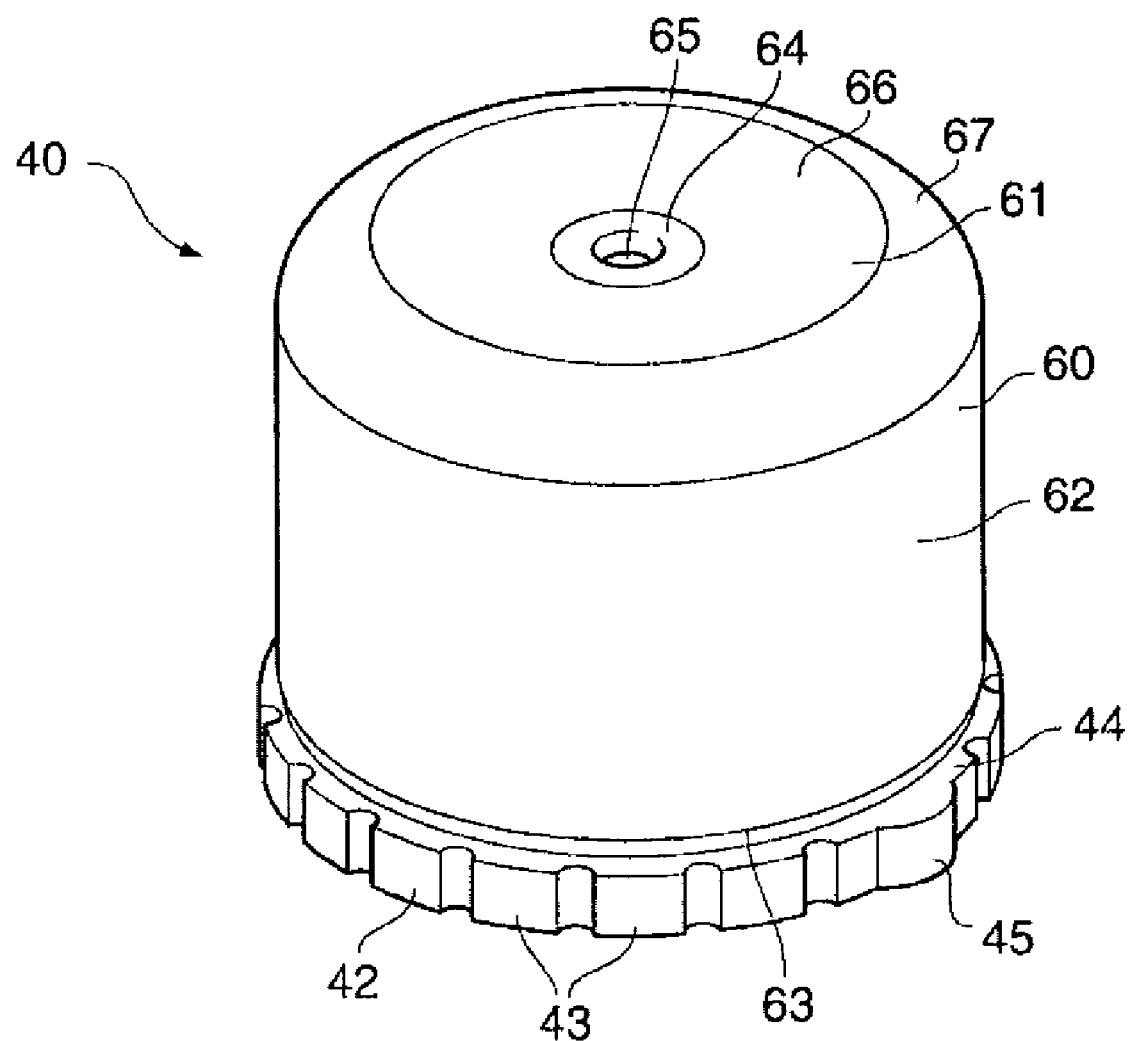
FIG. 6 is a perspective view of the cap of FIG. 4.
Figure 7:
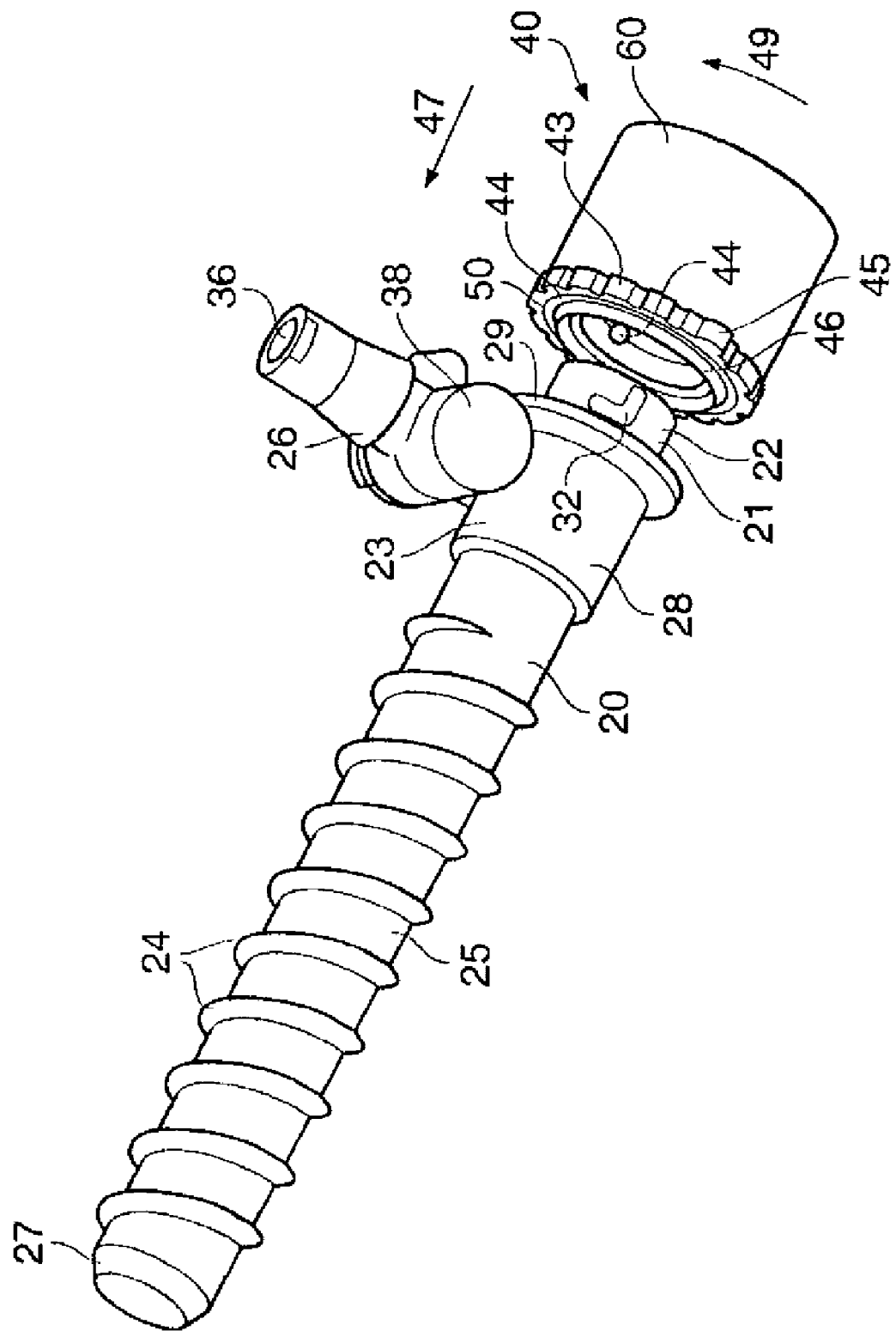
FIG. 7 is a perspective view of the cannula and removable cap of the assembly of FIG. 1 shown with the cap removed from the cannula.
Figure 8:
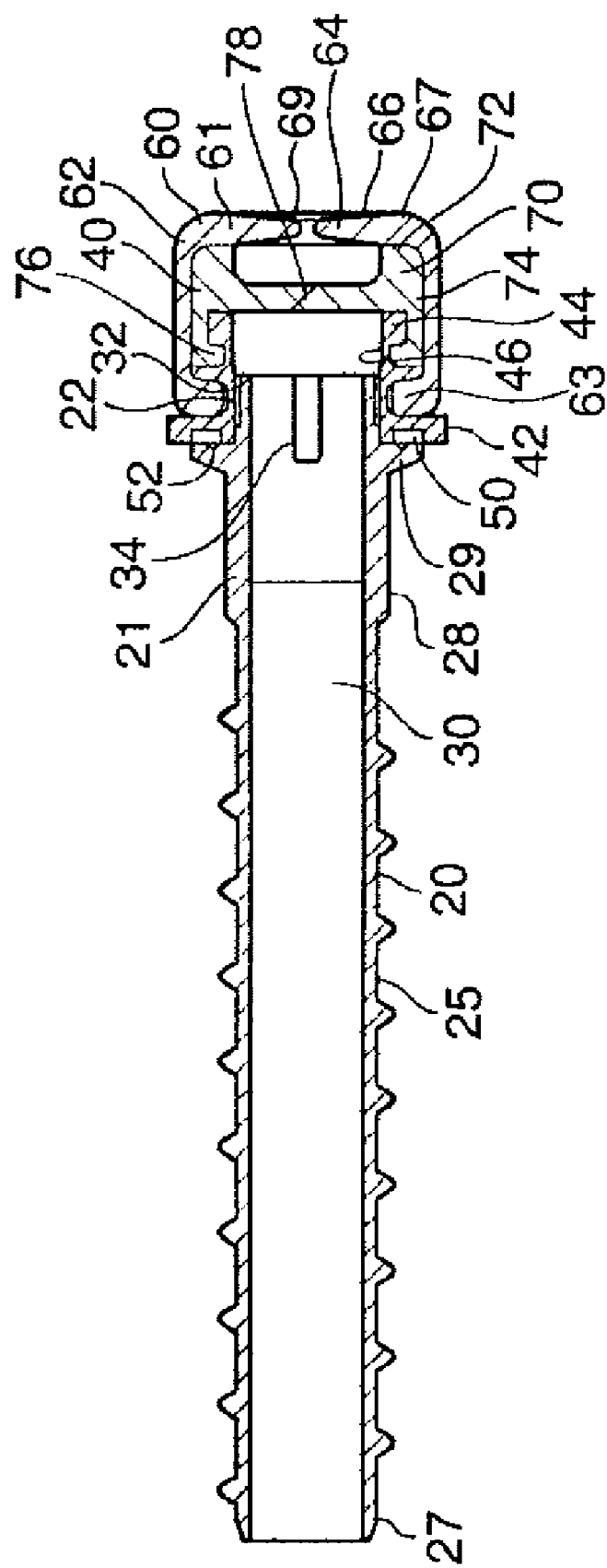
FIG. 8 is a cross-sectional view of the cannula and removable cap of the assembly of FIG. 1 shown with the cap coupled to the cannula.

Referring to FIGS. 4-6, cap 40 is assembled from three components: a mating member or body 44, an inner seal 70, and an outer seal 60. Mating member 44 has an inner wall 41 defining an opening 46 therethrough for receiving a surgical instrument, and a pair of projections 48 extending from wall 41 into opening 46. Projections 48 are sized and configured to interlock with J-shaped slots 32 defined in proximal portion 22 of cannula 20. As shown in FIGS. 7 and 8, cap 40 is coupled to cannula 20 by aligning projections 48 with J-shaped slots 32, pushing cap longitudinally in the direction of arrow 47 and then turning cap 40 in the direction of arrow 49 to lock cap 40 to cannula 20. Cap 40 will then lock itself in place in J-slots 32 by moving slightly in the direction opposite to arrow 47 due to the expansion of a compressed sealing member 50 (discussed below). Cap 40 is removable from cannula 20 by pushing cap 40 in the direction of arrow 47 to compress sealing member 50, turning cap 40 in a direction opposite to the direction of arrow 49 and pulling cap 40 in a direction opposite to the direction of arrow 47.

Mating member 44 includes a locking ring 42 having a plurality of knurls 43, which facilitate grasping cap 40 when coupling cap 40 to cannula 20 or removing cap 40 from cannula 20. Two of knurls 43 are enlarged knurls 45 aligned with projections 48, to facilitate aligning projections 48 with J-shaped slots 32. Mating member 44 is made of a material having a strength similar to the strength of cannula 20. For example, cannula 20 is made of a plastic material, such as polyester, having a tensile yield stress of approximately 45 MPa, while mating member 44 is made of a plastic material, such as acrylonitrile butadiene styrene (ABS) 2620 made by Dow Chemical, located in Midland, Mich., and having a tensile yield stress of approximately 41 MPa.

Mating member 44 includes a ring-shaped sealing member 50 that is integrally molded as a component of mating member 44, such that mating member 44 and sealing member 50 are a unitary piece. Sealing member 50 is composed of an elastomeric material that is chemically bonded with mating member 40. For example, sealing member 50 is composed of Versaflex® OM-9-802CL, manufactured by GLS Corporation of McHenry, Ill. Locking ring 42 has a flat face 58 with an indent 59 in which sealing member 50 is located. Sealing member 50 extends beyond flat face 58 to form an annular projection 52. Sealing member 50 also includes opposing lateral extensions 57 that facilitate molding sealing member 50 into mating member 44. As shown in FIG. 8, when cap 40 is coupled to cannula 20, sealing member 50 abuts against annular shoulder 27 of cannula 20, and annular projection 52 is compressed to form a fluid-tight seal between cap 40 and cannula 20. Because sealing member 50 is an integrally molded component of mating member 44, cap 40 can easily be coupled to and decoupled from cannula 20 without sealing member 50 becoming separated from cap 40 and dropped or misplaced.

Inner wall 41 of mating member 44 defines two annular grooves 54 and 56, for receiving inner seal 70 and outer seal 60, respectively, in a snap-fit. Inner seal 70 includes a middle section 77 defining a diagonal slit 78 for passing a surgical instrument therethrough, a wall 72 defining an open region 71 for receiving the surgical instrument, and an annular depending skirt 74 defining an open region 73 and including an inwardly projecting rib 76. Inner seal 70 snap-fits over mating member 44 with mating member 44 in open region 73 and inwardly projecting rib 76 received in annular groove 54, thus forming a fluid tight seal therebetween. Slit 78 permits surgical instruments to be passed through top wall 72 of inner seal 70 while limiting fluid leakage from cap 40.

Outer seal 60 includes a wall 61 and an annular depending skirt 62 defining an open region 69 and including an inwardly projecting rib 63. Outer seal 60 snap-fits over inner seal 70 and over mating member 44 with inner seal 70 in open region 69 and inwardly projecting rib 63 received in bottom annular groove 56, thus forming a second fluid tight seal with mating member 44.

Inner seal 70 and outer seal 60 are composed of an elastomeric material, such as 30-50 durometer liquid injection molded silicone. Wall or member 61 of outer seal 60 includes an inner ring 64 defining an aperture 65 therethrough, a tapered ring 66 surrounding inner ring 64, and a peripheral ring 67 surrounding tapered ring 66. Peripheral ring 67 has a constant thickness $T_1$, except for the region of chamfered surface 79. Tapered ring 66 tapers from thickness $T_1$ to a thickness $T_2$ that is less than $T_1$. Inner ring 64 is thickened along the outer side of seal 60 to form a reinforcing rib 68, such that inner portion has a thickness $T_3$ that is greater than $T_2$ and less than $T_1$. For example, $T_1$ is approximately 2.5 mm, $T_2$ is approximately 1 mm, and $T_3$ is approximately 1.5 mm. Tapered ring 66 is tapered on the outer surface of seal 60 at an angle of approximately 6 degrees over a length $L_1$ of approximately 6 mm. Tapered ring 55 is tapered on the inner surface of seal 60 at an angle of approximately 10 degrees. Reinforcing rib 68 has a length $L_2$ of approximately 1.5 mm. Aperture 65 allows surgical instruments to be passed through outer seal 60 while maintaining a seal to limit fluid leakage from cap 40. Tapered ring 66 increases the flexibility of outer seal 60 to allow introduction of a surgical instrument therethrough while thickened reinforcing rib 68 limits tearing of outer seal 60.

Figure 9:
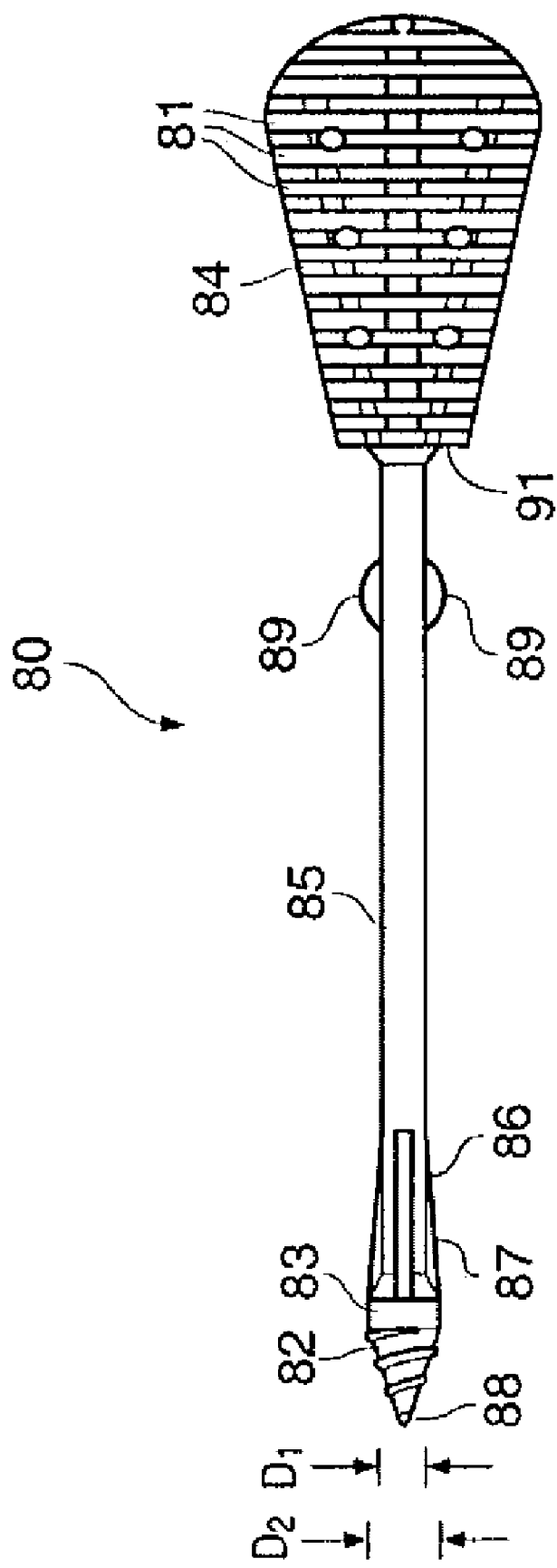
FIG. 9 is a side view of an obturator of the assembly of FIG. 1.

Referring to FIG. 9, obturator 80 includes distal end 82, an intermediate portion 83, an elongated body or shaft portion 85, and proximal handle 84. Handle 84 includes a plurality of cut-outs 81 that make handle 84 lighter in weight. Intermediate portion 83 has a diameter $D_2$ that is the same as or slightly less than the diameter of bore 30 in order to form a seal that inhibits tissue from entering bore 30 while obturator 80 and cannula 20 are being inserted into tissue. Shaft portion 85 has a diameter $D_1$ that is the same as or less than the diameter of cannula bore 30, in order reduce the weight of obturator 80 and to limit the stretching of outer seal 60 in cap 40 when shaft portion 85 is passed through cap 40. Shaft portion 85 has a distal portion 86 including a plurality of lateral flanges 87 that taper proximally in diameter from $D_2$ to $D_1$ for a smooth transition between the different diameters of intermediate portion 83 and shaft portion 85. Distal end 82 tapers from diameter $D_2$ of intermediate portion 83 to a distal point 88 to facilitate enlarging portal 92 (FIG. 1) in tissue 90. Distal end 82 is threaded to cooperate with threads 24 on cannula 20 to facilitate inserting cannula 20 into tissue 90.

Figure 10:
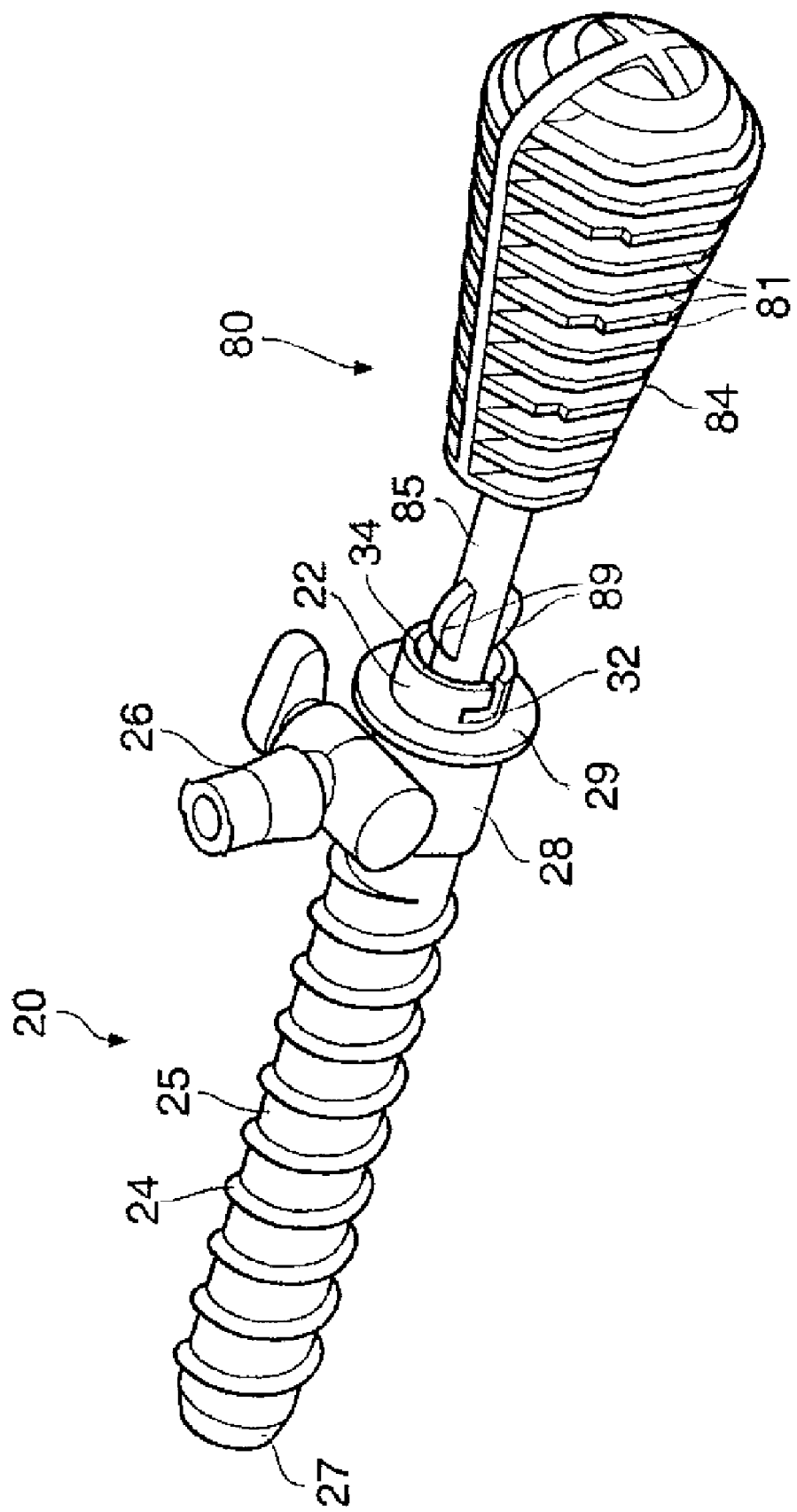
FIG. 10 is a perspective view of the cannula and obturator of the assembly of FIG. 1 shown without the cap.
Figure 11:
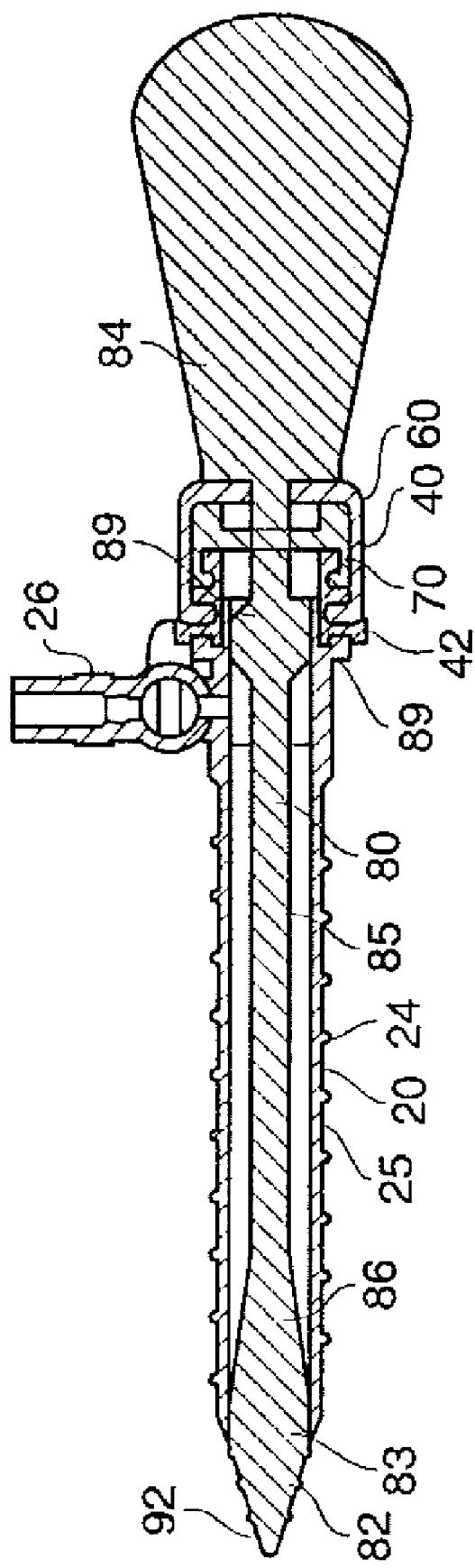
FIG. 11 is a cross sectional view of the assembly of FIG. 1 along line 11-11.

Referring also to FIGS. 10 and 11, shaft portion 85 includes opposed lateral wings or protrusions 89 that are sized and configured to be received in longitudinal slots 34 in cannula 20 when obturator 80 is inserted into cannula 20. Lateral wings 89 releasably couple obturator 80 to cannula 20 so that when obturator 80 is rotated by turning handle 84, cannula 20 rotates with obturator 80 to facilitate inserting cannula 20 into tissue 90.

Distal end 82 has a length of approximately 5 to 11.5 mm and is tapered at an angle of approximately 17.5 degrees to the center line. The threads on distal end 82 have a depth of approximately 0.5 to 1 mm, an angle of approximately 60 degrees and there are approximately 0.25 threads per mm. Intermediate portion 83 has a length of approximately 3 to 5 mm and a diameter $D_2$ of approximately 2.5 to 10 mm. Shaft portion 85 has a length of approximately 65 to 220 mm and a diameter of approximately 2.5 to 5.5 mm. Wings 89 are located on shaft portion 85 approximately 16.5 mm from a base 91 of handle 84.

In use, referring to FIG. 1, with cap 40 coupled to proximal end 22 of cannula 20 and obturator 80 located in cannula bore 30 with lateral wings 89 received in longitudinal slots 34, the user inserts threaded distal tip 82 of obturator 80 into a small incision or portal 92 that has been made in tissue 90 to form a channel 95 in tissue 90. The user then rotates handle 80 clockwise, inserting threaded distal portion 25 of cannula 20 into tissue 90.

Once distal portion 25 of cannula 20 is inserted into tissue 90, the user removes obturator 80 from tissue 90 and cannula 20 by pulling handle 84 while holding cannula 20 in place in tissue 90. Fluid can be aspirated or suction can be applied through cannula 20 by attaching a source of fluid or suction to port 36 of stopcock 26 and adjusting the opening of valve 38. The user passes surgical instruments into tissue 90 by passing them through outer seal 60, inner seal 70, and bore 30 in cannula 20 to perform an arthroscopic, endoscopic, or laproscopic surgical procedure. Outer seal 60 and inner seal 70 form a seal around the surgical instrument when the surgical instrument is located within cannula 20, and seal off cannula 20 when no surgical instrument is located therein.

During the surgical procedure, the user can remove cap 40 from cannula 20, e.g., to permit tissue that is too large to pass through cap 40 to be removed through cannula 90. The user can reattach cap 40 to cannula 20 to again provide the sealing function of cap 40. Cap 40 can be removed and reattached to cannula 20 as many times as desired during a surgical procedure. Once the user has completed the surgical procedure, the user removes cannula 20 from tissue 90 by rotating cannula counterclockwise.

A number of embodiments of the invention have been described. Nevertheless, it will be understood that various modifications may be made without departing from the spirit and scope of the invention. For example, the cannula can have a smooth outer surface rather than being threaded. The cannula also can have a valve other than a stopcock for aspirating fluid and applying suction. The distal threaded portion and the bore therethrough need not be tapered, e.g., when the cannula is manufactured by machining. The cannula can include more than two protrusion receiving formations. The protrusion receiving formations can be formed on an outer surface of the cannula.

The cap can be releasably coupled to the proximal end of the cannula by a mechanism other than a J-lock, such as a quick release or a spring loaded ball with a detent. The cap can be aligned with the cannula by other than an enlarged knurl on locking ring, such as by printed material or engraved lines on the cap. The cap can include protrusion receiving formations for receiving corresponding protrusions on the obturator to facilitate turning the cap and cannula assembly by turning the obturator. The cap can be tethered to the cannula, such as by a flexible tie, to avoid losing cap when it is detached from the cannula. The cap can include a smaller or larger number of seals to limit leakage of fluid when a surgical instrument is inserted therethrough. The integral sealing member can be mechanically attached to the mating member, such as be forming pin holes through the mating member and the sealing member including rod shaped projections extending through the pin holes and each being capped with a head.

The inner seal and outer seal can be attached to the cylindrical member by other than a snap-fit, such as by an adhesive. The inner seal can have an opening other than the slit therethrough, such as a circular or oblong aperture. The aperture through outer seal can have a shape other than circular, such as an elongated slot. The reinforcing rib on the outer seal can be on the inner side or the outer side of the outer seal, or both. The top wall of the outer seal also can include two or more reinforcing ribs surrounding the aperture. The top wall of the outer seal also can be of constant thickness.

The obturator can be of constant diameter throughout. The obturator can include a smaller or larger number of lateral projections that correspond to an equal or greater number of longitudinal slots inside the cannula. Other types of interlocking mechanisms between the obturator and the cannula can be used. The distal end of the obturator can be smooth and the handle can be solid.

In addition to the materials discussed above, the cannula, the cylindrical member, and the obturator can be made from any rigid biocompatible material such as a plastic, a metal, or a ceramic. Similarly, the integral seal, the inner seal, and the outer seal can be made of any elastomeric material such as latex or rubber.

In use, the obturator can be inserted into the cannula with the cap removed when the cannula is being inserted into the tissue. The obturator can be reinserted into the cannula at the end of the surgical procedure to facilitate removing the cannula from the tissue. These and other embodiments are within the scope of the following claims.

What is claimed is:

1. A medical assembly, comprising:
a shaft including a protrusion; and
a cannula having a wall with an inner surface defining a lumen for receiving the shaft and an outer surface, the inner surface defining a protrusion receiving formation extending from a proximal end of the cannula toward the distal end of the cannula and extending from the inner surface toward the outer surface only partially through the wall and the outer surface comprising a pair of outer slots, the outer slots being diametrically opposed with respect to the outer surface, the protrusion receiving formation and the outer slots at different radial locations around a proximal portion of the cannula.

2. The medical assembly of claim 1 wherein the protrusion receiving formation comprises a slot.

3. The medical assembly of claim 1 wherein the shaft includes a second, opposing protrusion and the inner surface defines a second, opposing protrusion receiving formation.

4. The medical assembly of claim 3 wherein the second protrusion receiving formation comprises a slot.

5. The medical assembly of claim 4 wherein the second protrusion receiving formation extends from the proximal end of the cannula.

6. The medical assembly of claim 1 wherein the lumen has a constant diameter.

7. The medical assembly of claim 1 wherein the lumen is tapered.

8. A medical cannula comprising:
a wall with an inner surface defining a lumen and an outer surface, the inner surface defining a protrusion receiving formation extending from a proximal end of the cannula toward the distal end of the cannula, and extending from the inner surface toward the outer surface only partially through the wall, the outer surface comprising an outer slot, the protrusion receiving formation and the outer slot at different radial locations around a proximal portion of the cannula.

9. The medical cannula of claim 8 wherein the protrusion receiving formation comprises a slot.

10. The medical cannula of claim 8 wherein the inner surface defines a second, opposing protrusion receiving formation.

11. The medical cannula of claim 10 wherein the second protrusion receiving formation comprises a slot.

12. The medical cannula of claim 10 wherein the second protrusion receiving formation extends from the proximal end of the cannula.

13. The medical cannula of claim 8 wherein the outer slot is J-shaped.

14. The medical cannula of claim 8 wherein the outer surface defines a second, opposing outer slot.

15. The medical cannula of claim 14 wherein the second outer slot is J-shaped.

16. The medical cannula of claim 8 further comprising an annular shoulder coupled to the wall for forming a fluid-tight seal with a cap.

17. The medical cannula of claim 8 wherein the wall has an outer surface that is threaded.

18. The medical cannula of claim 8 wherein the lumen has a constant diameter.

19. The medical cannula of claim 8 wherein the lumen is tapered.

20. The medical cannula of claim 15, wherein the outer slots are configured for receiving protrusions extending from a cap, the outer slots being diametrically opposed with respect to the outer surface.

21. The medical cannula of claim 20 further comprising the cap having the protrusions extending from an inner surface of the cap.

22. A medical cannula comprising:
a wall having an outer surface and an inner surface, wherein the inner surface defines a lumen and a protrusion receiving formation extending from the inner surface toward the outer surface only partially through the wall and shaped to receive a protrusion therein, and the outer surface defines an outer slot, the protrusion receiving formation and outer slot at different radial locations around a proximal portion of the cannula.

* * * * *